United States Patent [19]

Watanabe et al.

[11] 4,170,531

[45] Oct. 9, 1979

[54] METHOD OF PRODUCING AN OXYGEN CONCENTRATION CELL

[75] Inventors: Tetsuo Watanabe, Nagoya; Shigetaka Wada, Kuwana; Shunzo Mase, Tobishima, all of Japan

[73] Assignee: NGK Insulators, Ltd., Nagoya, Japan

[21] Appl. No.: 872,636

[22] Filed: Jan. 26, 1978

[30] Foreign Application Priority Data

Jan. 31, 1977 [JP] Japan .................................. 52-8717

[51] Int. Cl.$^2$ ............................................ G01N 27/46
[52] U.S. Cl. .............................. 204/195 S; 427/125; 427/126; 429/33
[58] Field of Search ............... 204/15, 195 S; 429/33; 427/126, 125

[56] References Cited

U.S. PATENT DOCUMENTS 3,978,006  8/1976  Topp et al. ..................... 204/195 S

OTHER PUBLICATIONS

"SAE Paper 750,223", Ceramic Aspects of the Bosch Lamda-Sensor, 1975, pp. 1-18.

*Primary Examiner*—T. Tung
*Attorney, Agent, or Firm*—Stevens, Davis, Miller & Mosher

[57] ABSTRACT

A simple method of producing an oxygen concentration cell provided with durable electrodes having a high activity and a low internal resistance is disclosed. The method comprises applying a solution of a compound of platinum group metal to an oxygen ion conductive solid electrolyte, converting the compound into an insoluble or hardly soluble compound by a chemical reaction, and thermally decomposing the insoluble or hardly soluble compound into the platinum group metal to be used as the electrodes of the cell.

2 Claims, No Drawings

METHOD OF PRODUCING AN OXYGEN CONCENTRATION CELL

BACKGROUND OF THE INVENTION (1) Field of the Invention

The present invention relates to a method of producing an oxygen concentration cell which makes use of oxygen ion conductive solid electrolyte.

(2) Description of the Prior Art

There has been well known an oxygen concentration cell consisting of a partition wall made of oxygen ion conductive solid electrolyte, such as stabilized zirconia or the like, and electrically conductive electrodes applied to both of the opposite surfaces of the wall. It is widely known that this oxygen concentration cell is used for the measurement of oxygen partial pressure in the waste gas of boiler or in the exhaust gas of motor car, and is used as a fuel cell for the direct generation of electricity. When the oxygen concentration cell is used for the above described purposes, it is very important that the electrodes of the cell are formed of durable electrodes having a high activity and a low internal resistance.

In general, porous platinum group metals are used as a material for the electrodes of the oxygen concentration cell of this kind.

As the method of applying the porous electrodes formed of platinum group metal to the solid electrolyte, chemical plating method, physical plating method, baking method and the like are known. However, the electrode formed by the chemical plating method has the serious drawbacks that the electrode is poor in durability due to its poor adhesion to the solid electrolyte, and that since the electrode is formed into a filmly layer, the electrode is low in the gas permeability and activity. The electrode formed by the physical plating methods, such as vapor deposition, sputtering, ion plating and the like, has the drawbacks that an expensive physical plating apparatus, which has a complicated structure and is poor in workability, must be used, that the material for the electrode is wastefully adhered to the inner wall or the like of the apparatus, and that since the electrode is formed into a filmy layer, the electrode is poor in gas permeability and in activity and is not sufficient in durability.

Further, the electrode formed by the baking method, wherein a paste formed of platinum powder is applied to the solid electrolyte and baked thereto, has the drawbacks that the electrode has a high internal resistance, and that when a paste containing glass component is used, the activity of the electrode is low, while when a paste containing no glass component is used, the electrode is poor in adhesion to the solid electrolyte and in durability.

Recently, a method of forming electrodes has been proposed, wherein the surfaces of a solid electrolyte are roughed to form coarse surfaces, a solution of platinate is impregnated into pores of the coarse surfaces, and the platinate is reduced to form the electrodes. However, in this method, since the diffusion velocity of gas into the platinum phase deposited in the pores on the solid electrolyte surface is low, the response speed of variation of electromotive force against the variation of oxygen partial pressure in a gas to be measured is low where the resulting cell is used for the measurement of oxygen partial pressure. Further, during the platinate applied to the solid electrolyte in the form of a solution is reduced, the platinate solution tends to flow down, and a platinum layer having a uniform thickness or a thick platinum layer can not be obtained.

SUMMARY OF THE INVENTION

An object of the present invention is to provide a method capable of producing an oxygen concentration cell without the above described drawbacks of conventional methods.

Another object of the present invention is to provide a simple methode of producing an oxygen concentrationcell provided with durable electrodes having a high activity, a high response speed of the variation of electromotive force and a low internal resistance.

The feature of the present invention consists in a method of producing an oxygen concentration cell, comprising applying a solution of a compound of platinum group metal to an oxygen ion conductive solid electrolyte, converting the compound of platinum group metal into an insoluble or hardly soluble compound by a chemical reaction, and thermally decomposing the insoluble or hardly soluble compound into the platinum group metal to be used as the electrodes of the cell.

DETAILED DESCRIPTION OF THE INVENTION

The present invention will be explained in more detail hereinafter.

As the oxygen ion conductive solid electrolyte, use is made of sintered articles of zirconium oxide stabilized with calcium oxide, yttrium oxide or ytterbium oxide, sintered articles of cerium oxide containing lanthanum oxide, and sintered articles of these oxides added with conventional sintering aids, such as aluminum oxide and the like.

As the solution of a compound of platinum group metal, use is made of aqueous solution, hydrochloric acid solution, ethanol solution and the like of platinum tetrachloride, hexachlorplatinic acid, hexammineplatinum chloride, palladium sulfate, rhodium sulfate or the like. Among them, aqueous solution of platinum tetrachloride or hexachloroplatinic acid or the aqueous solution containing hydrochloric acid is preferably used. The solution of the compound of platinum group metal can be applied to the solid electrolyte surface by any of coating, spraying and dipping processes.

As the method of converting the compound of platinum group metal in the solution form into an insoluble or hardly soluble compound by a chemical reaction, the following methods may be adopted. The solid electrolyte applied with the solution of the compound of platinum group metal is contacted with ammonia or amine in gaseous phase, or is sprayedwith a solution of ammonia or amine, whereby the ammonia or amine is reacted with the solution of the compound of platinum group metal. Further, the thickness of the electrode can be increased by applying platinum powder and the like to the electrode formed by the method of the present invention, and baking the powder ot the electrode.

The reason why durable electrode having a high activity and a low internal resistance can be produced according to the present invention is probably as follows. A solution of a compound of platinum group metal, for example, an aqueous solution of platinum tetrachloride, which has fully wet the fine concave and convex portions on a solid electrolyte surface, is exposed to ammonia gas, whereby the platinum tetrachloride is converted into fine crystals of ammonium hexachloroplatinate uniformly adhered to the solid electrolyte surface, and a platinum layer having a large surface area is formed by a thermal decomposition of the ammonium hexachloroplatinate. Particularly, when an aqueous solution of platinum tetrachloride or hexachloroplatinic acid is used, since these solutions have a high penetration ability, the concave and convex portions of the solid electrolyte surface can be easily and fully wet by these solutions, and further since these solutions are strongly acidic, the solid electrolyte surface is somewhat corroded by these solutions, and as a result the adhering strength of the platinum layer to the solid electrolyte surface is improved.

The following examples are given for the purpose of illustration of this invention and are not intended as limitations thereof.

EXAMPLE 1

A powdery mixture consisting of 90% by weight of zirconium oxide, 7% by weight of calcium oxide and 3% by weight of aluminum oxide was pressed and fired at 1,700° C. to produce a solid electrolyte disk having a diameter of 20 mm and a thickness of 1 mm. This disk had a density of 5.26 g/cm$^3$ and a water absorption of 0.01%. An aqueous solution of platinum tetrachloride having a platinum content of 0.2 g per cum$^3$ was applied to both surfaces of the disk, and concentrated ammonia water was sprayed thereon, and then the above treated disk was fired at 1,200° C. The above described procedures of the application of the aqueous solution of platinum tetrachloride, the spraying of ammonia water and the firing of the disk were repeated 5 times to form platinum electrodes on the disk, whereby an oxygen concentration cell of the present invention was obtained. The resulting electrode of the oxygen concentration cell had a surface electric resistivity of 0.3 Ω per square. The durability of the electrode was evaluated by heating the oxygen concentration cell for 1,000 hours in an electric furnace kept at 1,000° C. in air. The property of the oxygen concentration cell was evaluated by the internal resistance and the response speed of the electrode against the variation of oxygen partial pressure. The internal resistance was measured by the two terminal method in air kept at 500° C.

When an oxygen concentration cell is kept at 500° C. and one of the electrode surfces is contacted with air and another electrode surface is firstly contacted with air and then contacted with a nitrogen atmosphere containing 5% of hydrogen, the electromotive force generated between the electrodes on both surfaces of the oxygen concentration cell varies from 0 volt to about 1 volt. The variation speed (response speed) of this electromotive force varis depending upon the activity of the electrodes. In the present invention, the activity of electrodes was evaluated in the following manner. The contacting atmosphere of one electrode surface was changed from air to a nitrogen atmosphere containing 5% of hydrogen, and a time required to vary the electromotive force from 0 volt to 0.5 volt was measured.

The internal resistance and the variation time of the electromotive force of the above obtained cell were measured before and after the cell was heat treated at 1,000° C. for 1,000 hours. The obtained results are shown in the following Table 1 together with the results obtained in the following Examples 2–4 and Comparative examples 1–4. As seen from Table 1, the cell obtained in this Example 1 had an internal resistance of 2.7 kΩ before the heat treatment and an internal resistance of 4.9 kΩ after the heat treatment, and had a variation time of the electromotive force of 1.4 seconds before the heat treatment and a variation time of the electromotive force of 1.6 seconds after the heat treatment.

For comparison, an oxygen concentration cell of Comparative example 1 was produced under the same condition as described above, except that the spraying of concentrated ammonia water was omitted. However, this comparative cell is higher in the internalresistance and is no longer in the variation time of the electromotive force than the cell of Example 1 in both of the values before and after the heat treatment at 1,000° C. for 1,000 hours. Therefore, the oxygen concentration cell of Comparative example 1 was inferior to that of Example 1.

EXAMPLE 2

A powdery mixture consisting of 93% by weight of zirconium oxide and 7% by weight of calcium oxide was pressed and fired at 1,800° C. to producea solid electrolyte disk having a diameter of 20 mm and a thickness of 1 mm. This disk had a density of 5.11 g/cm$^3$ and a water absorption of 0.01%. An aqueous solution of palladium nitrate having a palladium content of 0.2 g per cm$^3$ was applied to both surfaces of the disk, and the disk was left to stand for 10 minutes in a space above ammonia water contained in a vessel, and then the above treated disk was fired at 1,200° C. The above described procedures of the application of the aqueous palladium nitrate solution, the treatment with ammonia and the firing at 1,200° C. of the disk were repeated 2 times. Then, a paste formed of platinum powders added in water was applied to the above treated disk, and the disk was fired at 1,200° C. to produce an oxygen concentration cell. The resulting oxygen concentration cell had a surface electric resistivity of 0.1 Ω per square. The internal resistance of the cell and the activity of the electrode were measured in the same manner as described in Example 1 before and after the cell was heated at 1,000° C. for 1,000 hours.

The above obtained oxygen concentration cell was superior to an oxygen concentration cell of Comparative example 2, which was produced under the same condition as described above, except that the step for placing the disk in the space of a vessel containing ammonia water was omitted, as shown in Table 1.

EXAMPLE 3

A powdery mixture consisting of 84% by weight of zirconium oxide, 14% by weight of yttrium oxide and 2% by weight of kaolin was pressed and fired at 1,700° C. to produce a solid electrolyte disk having a diameter of 20 mm and a thickness of 1 mm. The disk had a density of 5.57 g/cm$^3$ and a water absorption of 0.01%. The disk was subjected to the treatment effected repeatedly 4 times, in which treatment an aqueous solution of hexachloroplatinic acid having a platinum content of 0.3 g per cm$^3$ was applied to both surfaces of the disk and diethylamine was sprayed on the disk and then the above treated disk was fired at 1,200° C., to produce an oxygen concentration cell provided with electrodes according to the present invention.

For comparison, an oxygen concentration cell of Comparative example 3 was produced under the same condition as described above, except that the step for spraying diethylamine was omitted. The internal resistance and electrode activity of the resulting oxygen concentration cells were measured in the same manner as described in Example 1 before and after the cells were heat treated at 1,000° C. for 1,000 hours.

It can be seen from Table 1 that the oxygen concentration cell of Example 3 is superior to that of Comparative example 3 in both internal resistance and electrode activity.

The internal resistance and the response speed against the variation of oxygen partial pressure of the above obtained oxygen concentration cells were measured in the same manner as described in Example 1 before and after the cells were heat treatment at 1,000° C. for 1,000 hours. It can be seen from Table 1 that the oxygen concentration cell of Example 4 is superior to that of Comparative example 4.

Table 1

|  |  | Before heat treatment | | After heat treated at 1,000° C. for 1,000 hours | |
|---|---|---|---|---|---|
|  |  | Internal resistance (kΩ) | Variation time of electromotive force (sec.) | Internal resistance (kΩ) | Variation time of electromotive force (sec.) |
| Method of the present invention | Example 1 | 2.7 | 1.4 | 4.9 | 1.6 |
|  | Example 2 | 3.2 | 1.7 | 5.5 | 2.3 |
|  | Example 3 | 1.1 | 1.3 | 2.1 | 1.6 |
|  | Example 4 | 0.8 | 1.3 | 1.8 | 1.5 |
| Comparative method | Comparative example 1 | 6.6 | 2.7 | 17.3 | 4.3 |
|  | Comparative example 2 | 8.7 | 4.1 | 18.1 | 9.0 |
|  | Comparative example 3 | 4.7 | 2.2 | 13.5 | 4.9 |
|  | Comparative example 4 | 4.1 | 2.4 | 11.0 | 4.1 |

EXAMPLE 4

A powdery mixture consisting of 84% by weight of zirconium oxide and 16% by weight of yttrium oxide was pressed and fired at 1,800° C. to produce a solid electrolyte disk having a diameter of 20 mm and a thickness of 1 mm. The disk had a density of 5.62 g/cm$^3$ and a water absorption of 0.01%. The disk was subjected to the treatment effected repeatedly 4 times, in which treatment an aqueous solution of platinum tetrachloride having a platinum content of 0.4 g per cm$^3$ was applied to both surfaces of the disk, and the disk was left to stand for 10 minutes in a space above ammonia water contained in a vessel and then the above treated disk was fired at 1,000° C., to produce an oxygen concentration cell provided with platinum electrodes according to the present invention.

For comparison, an oxygem concentration cell of Comparative example 4 was produced under the same condition as described above, except that the step for leaving the disk to stand in a vessel containing ammonia water was omitted.

It can be seen from the above described Examples that, according to the present invention, oxygen concentration cells having a low internal resistance, a high electrode activity and a high resistance against the deterioration due to the lapse of time at high temperature can be obtained. Further, the cells have excellent performance as sensors for measuring osygen partial pressure and as fuel cells, and are very useful for industry.

What is claimed to:

1. A method of producing an oxygen concentration cell, comprising applying a solution of a compound a platinum group metal to an oxygen on conductive solid electrolyte, converting the compound of platinum group metal into an insoluble or hardly soluble compound by contacting the applied solution with ammonia or amine in the gaseous or liquid state, and thermally decomposing the insoble or hardly soluble compound into the platinum group metal to be used as the electrodes of the cell.

2. A method according to claim 1, wherein said solution of a compound of platinum group metal is an aqueous solution of platinum tetrachloride or hexachloroplatinic acid.

* * * * *